United States Patent

Wadhwani et al.

[11] Patent Number: 5,331,972
[45] Date of Patent: Jul. 26, 1994

[54] BONE MARROW BIOPSY, ASPIRATION AND TRANSPLANT NEEDLES

[75] Inventors: Suresh Wadhwani, Valencia; Greg Smith, Newhall, both of Calif.

[73] Assignee: Baxter International Inc., Deerfield, Ill.

[21] Appl. No.: 984,748

[22] Filed: Dec. 3, 1992

[51] Int. Cl.$^5$ ............................................. A61B 10/00
[52] U.S. Cl. ....................................................... 128/754
[58] Field of Search ........................ 128/749, 753, 754; 606/170

[56] References Cited

U.S. PATENT DOCUMENTS

| | | | |
|---|---|---|---|
| D. 289,198 | 4/1987 | Karten | D24/24 |
| 2,219,605 | 6/1938 | Turkel | |
| 3,587,560 | 6/1971 | Glassman | |
| 3,800,783 | 4/1974 | Jamshidi | 128/754 |
| 3,938,505 | 2/1976 | Jamshidi | |
| 4,142,517 | 3/1979 | Stravropoulos et al. | |
| 4,256,119 | 3/1981 | Gauthier | 128/754 |
| 4,306,570 | 12/1981 | Matthews | 128/754 |
| 4,403,617 | 9/1983 | Tretinyak | 128/754 |
| 4,469,109 | 9/1984 | Mehl | 128/753 |
| 4,513,754 | 4/1985 | Lee | 128/753 |
| 4,543,966 | 10/1985 | Islam et al. | 128/754 |
| 4,620,547 | 11/1986 | Boebel | 128/754 |
| 4,640,296 | 2/1987 | Schnepp-Pesch et al. | 128/754 |
| 4,681,123 | 7/1987 | Valtchev | 128/753 |
| 4,696,308 | 9/1987 | Meller et al. | 128/754 |
| 4,699,154 | 10/1987 | Lindgren | 128/754 |
| 4,702,261 | 10/1987 | Cornell et al. | 128/754 |
| 4,708,147 | 11/1987 | Haaga | 128/753 |
| 4,733,671 | 3/1988 | Mehl | 128/754 |
| 4,735,215 | 4/1988 | Goto et al. | 128/754 |
| 4,776,346 | 10/1988 | Beraha et al. | 128/754 |
| 4,776,847 | 10/1988 | Krebs | 128/754 |
| 4,781,202 | 11/1988 | Janese | 128/754 |
| 4,785,826 | 11/1988 | Ward | 128/754 |
| 4,793,363 | 12/1988 | Ausherman et al. | 128/754 |
| 4,838,282 | 6/1989 | Strasser et al. | 128/754 |
| 4,850,373 | 7/1989 | Zatloukal et al. | 128/749 |
| 4,873,991 | 10/1989 | Skinner | 128/754 |
| 4,881,551 | 11/1989 | Taylor | 128/754 |
| 4,893,635 | 1/1990 | de Groot et al. | 128/754 |
| 4,903,709 | 2/1990 | Skinner | 128/754 |
| 4,907,599 | 3/1990 | Taylor | 128/754 |
| 4,917,100 | 4/1990 | Nottke | 128/749 |
| 4,924,878 | 5/1990 | Nottke | 128/751 |
| 4,926,877 | 5/1990 | Bookwalter | 128/754 |
| 4,958,625 | 9/1990 | Bates et al. | 128/754 |
| 4,976,269 | 12/1990 | Mehl | 128/754 |
| 4,989,614 | 2/1991 | Dejter, Jr. et al. | 128/752 |
| 4,991,600 | 2/1991 | Taylor | 128/754 |
| 5,005,585 | 4/1991 | Mazza | 128/754 |
| 5,012,818 | 5/1991 | Joishy | 128/754 |
| 5,014,717 | 5/1991 | Lohrmann | 128/754 |
| 5,036,860 | 8/1991 | Leigh et al. | 128/754 |
| 5,040,542 | 8/1991 | Gray | 128/754 |
| 5,048,538 | 9/1991 | Terwilliger et al. | 128/754 |
| 5,056,529 | 10/1991 | de Groot | 128/754 |
| 5,060,658 | 10/1991 | Deiter, Jr. et al. | 128/753 |
| 5,080,655 | 1/1992 | Haaga | 128/754 |
| 5,090,419 | 2/1992 | Palestrant | 128/754 |
| 5,125,413 | 6/1992 | Baran | 128/754 |
| 5,127,419 | 7/1992 | Kaldany | 128/754 |
| 5,133,359 | 7/1992 | Kedem | 128/754 |

OTHER PUBLICATIONS

Popper & Sons, Inc. product catalog, pp. 16B & 29B (New Hyde Park, N.Y. 11040) Dec. 2, 1993.

*Primary Examiner*—Max Hindenburg
*Attorney, Agent, or Firm*—Kay H. P. Hannafan; Paul C. Flattery

[57] ABSTRACT

Novel bone-marrow biopsy, aspiration and transplant needles are described having several unique features. One unique feature is an offset handle which allows a user to use their index finger to guide a needle into a patient. Another unique feature is a cannula which has multiple cutting teeth that can be used to cut bone when the cannula is axially rotated. Yet another unique feature is a stylet with a highly effective cutting tip.

7 Claims, 6 Drawing Sheets

BONE MARROW BIOPSY, ASPIRATION AND TRANSPLANT NEEDLES

TECHNICAL FIELD

The invention relates generally to the field of medical instruments, and more particularly to those instrument employed in biopsy, aspiration, and transplant procedures of bone marrow.

BACKGROUND ART

In the medical field, it is frequently desirable to take biopsy samples from a patient. Two major fields of biopsy procedures exist. One field is known as "soft-tissue biopsy" and the other field is known as "bone marrow biopsy". In the bone marrow biopsy field, it is always necessary to puncture the bone of a patient in order to retrieve bone marrow which normally exists only in the center of a bone.

It may be desirable to retrieve bone marrow for several different reasons. In one type of bone marrow procedure, it is desirable to retrieve a "core" of bone marrow to examine bone marrow architecture. This procedure may be useful in determining whether a patient has cancer and the extent of cancerous cells that may exist. Examining a bone marrow core typically involves an extended period of time in which the core is first prepared and then sliced into thin samples which are examined under a microscope.

In other bone marrow procedures, it is desirable to simply aspirate a portion of the bone marrow to make a relatively rapid determination of the number of bone particles in the sample to indicate the state of a patient's disease. Aspirated bone marrow can be further studied to aid in the diagnosis of a patient.

Finally, in other bone marrow procedures, multiple aspirations of bone marrow are conducted to perform a bone marrow transplant. While each of these procedures have different goals, they all require that the bone be punctured in order to access the bone marrow within. Thus, it is important to provide a needle which enhances the ability of the user to puncture bone with minimal trauma to the patient.

All bone marrow biopsy, aspiration and transplant needles currently on the market have a handle with a cannula extending outwardly from the handle. The handle is used by the doctor to apply force to the cannula as the cannula punctures the bone. Such needles typically include a stylet with a sharpened tip which is inserted through the cannula and is used to initially puncture the bone. The stylet is then removed and bone marrow is withdrawn from the patient by manipulating the cannula to cause bone marrow to move into the interior of the cannula. In some cases a slight suction is applied to the cannula to hold the bone marrow in place as the cannula is removed from the patient.

Bone marrow needles have traditionally been designed so that the needle is attached to the center of the handle. While many physicians feel comfortable with a centrally attached needle, it has been recently discovered that it may be easier to guide a needle with a users' index finger if the needle is not centrally located on the handle of the needle assembly. It has also recently been discovered that when an off-center device is used, it is important to insure that a physician's arm, wrist, and index finger are all generally in alignment with the cannula of the needle to provide enhanced control over the needle. These discoveries are discussed in greater detail below with regard to the present invention.

Also, bone marrow needle tips have traditionally been formed using a single angular grind which essentially produces a single cutting surface. Such a needle tip is described in U.S. Pat. No. 4,469,109. Refinements have been made to the needle tip over the years. For example, U.S. Pat. No. 4,838,282 describes a stylet and cannula in which the stylet extends beyond the length of a cannula and in which the stylet and cannula have angular surfaces which are parallel to one anther and, thus, mate with one another. While at least one other manufacturer has developed a cannula with more than one cutting surface, the cannula is intended to be used with a stylet that has cutting surfaces that are in direct alignment with the cutting surfaces of the cannula. The present invention seeks to improve upon the cutting features of both the stylet and of the cannula without requiring that the cutting surfaces of the cannula mate with the cutting surfaces of the stylet.

Another feature of most bone marrow needle assemblies currently on the market is that when the stylet is removed from the cannula, the shape of the handle typically is materially changed. For example, the bone marrow needle assembly described in U.S. Pat. No. 4,838,282 involves removing approximately half of the handle assembly when the stylet is removed from the cannula. It has recently been discovered, as part of the subject invention, that it is desirable to maintain the original shape of the handle as much as possible after the stylet has been removed to allow a physician to more easily manipulate the cannula within a patient's bone.

OBJECTS OF THE INVENTION

Thus, it is an object of the invention to provide a bone marrow needle assembly having an offset handle to assist a physician in inserting a needle into a patient.

It is another object of the invention to provide a bone marrow needle assembly having a stylet tip and a cannula tip which have increased cutting capability.

It is still another object of the invention to provide a bone marrow needle assembly having a handle design such that the shape of the handle remains essentially the same after the stylet has been removed.

These and other objects of the invention will now be described in greater detail with regard to the subject invention.

SUMMARY

A needle assembly is described which includes a handle and a cannula. The cannula has a first end connected to the handle and a second end extending outwardly from the handle. The second end of the cannula has multiple cutting teeth that can be used to cut bone when the cannula is axially rotated. In one embodiment of the invention a removable stylet is also provided which has first and second ends. The second end of the stylet extends beyond the second end of the cannula. In one embodiment, the second end of the stylet has a tip having first and second tip surfaces which form an obtuse angle. The tip also has first and second cutting surfaces located between each of the tip surfaces. The cutting surfaces form an acute angle with one another.

In a preferred embodiment of the invention the handle has an upper surface which has a downward extending off-center radius to conform to the shape of a user's palm. The off-center radius causes the handle to have a first relatively narrow end and a second relatively wide end. The handle also has a generally planar lower surface designed to be easily gripped by a user's fingers. In the preferred embodiment, the first end of the cannula is connected to the lower surface of the handle toward the relatively narrow end. Thus, when a user grips the handle, the user's index finger can be naturally applied to the cannula to guide the cannula into a patient. Also, the user's wrist and forearm are in general alignment with the user's index finger and the axis of the cannula.

Finally, in one embodiment, the removable stylet has a knob attached to a first end. The knob has an upper surface which has a downward extending off-center radius that is generally equal to the off-center radius of the handle. The handle is provided with a receiving orifice to receive the knob so that the upper surface of the knob mates with the curved upper surface of the handle.

SUMMARY OF THE INVENTION

Figure 1:
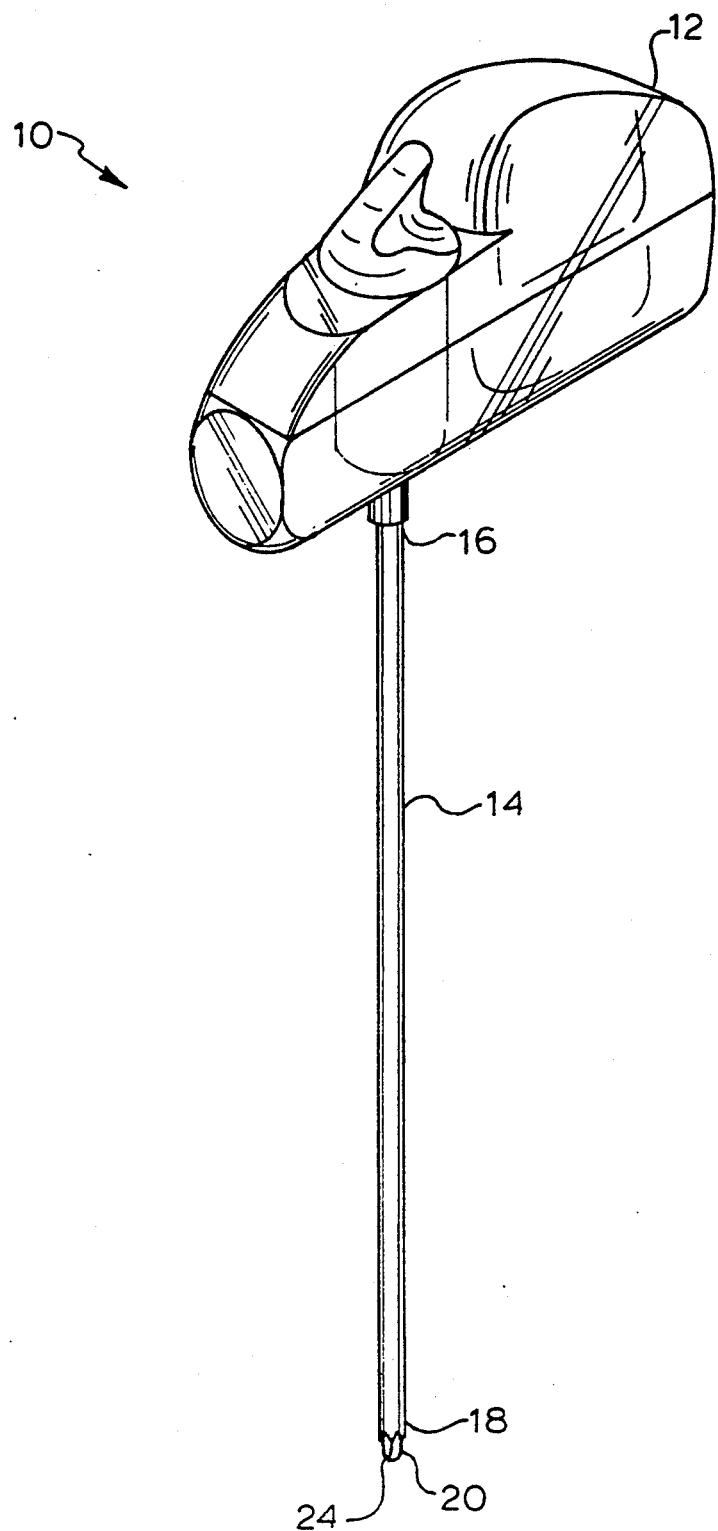
FIG. 1 is a perspective view of the preferred embodiment of the needle assembly of the subject invention.

Refer now to FIG. 1 which is a perspective view of the preferred embodiment of the needle assembly 10 of the subject invention. As can be seen in the figure, the assembly includes a handle 12 and a cannula 14. The cannula includes a first end 16 connected to the handle 12 and a second end 18 extending outwardly from the handle. The cannula 14 is a hollow tubular member. The first end 16 is permanently attached to the handle 12.

In the preferred embodiment, a removable stylet 20 having first and second ends 22, 24 is provided. In the preferred embodiment, the second end 24 extends beyond the second end 18 of the cannula.

Figure 2:
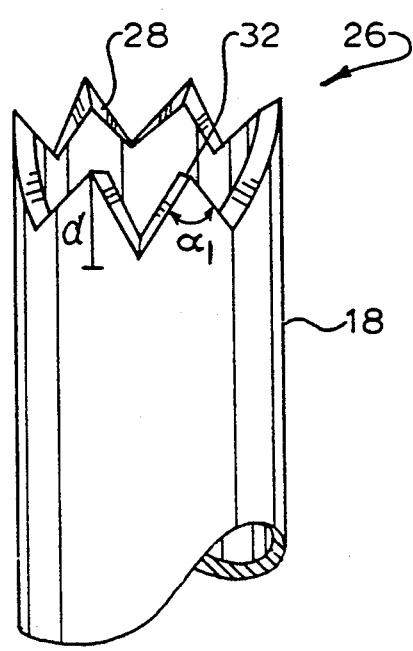
FIG. 2 is a perspective view of the cannula tip in one embodiment of the invention.

Refer now to FIG. 2 which is a perspective view of the second end 18 of the cannula in the preferred embodiment of the invention. As can be seen in the figure, the second end 18 has a tip 26 which includes multiple cutting teeth 28. The number of teeth may vary. In the preferred embodiment, the number of cutting teeth 28 ranges from four to twelve. In most embodiments, it is envisioned that six cutting teeth will be used as illustrated in FIG. 2. It is generally desirable that the angle $a_1$ formed by a tip 32 of a cutting tooth is approximately 60°. In general it is desirable that the angle of each cutting tooth be such that the depth d is relatively shallow. The number of teeth used in a particular cannula tip is related to the diameter of the cannula. Generally, the greater the diameter of the cannula the greater number of teeth will be need to produce a similar depth. In the preferred embodiment, the cutting teeth are sufficiently sharp to cause bone to be cut when the cannula is axially rotated back and forth.

One advantage of the cannula tip illustrated in FIG. 2 is that in some instances, the teeth may be sufficiently sharp to cut bone without the need of a stylet. In those cases, the bone marrow extraction procedure is simplified because a physician does not have to remove the stylet in the middle of a procedure. Yet another advantage of the cannula tip described in FIG. 2 is that in some instances, when cancer of the bone is suspected, it is desirable to obtain a sample of the bone itself rather than a sample of bone marrow. The cannula tip described in FIG. 2 is capable of cutting bone, and is thus capable of obtaining a bone sample. This feature is expected to be extremely significant.

Another advantage of the cannula tip described in FIG. 2 is that when the cannula is axially rotated back and forth within the bone, it is expected that it will be possible to obtain a very "clean" sample of bone marrow with minimal damage to the sample. In other more traditional types of bone marrow cannulas having only a single beveled edge, it is possible that more damage to the sample may occur than when using a cannula having numerous cutting teeth as illustrated in FIG. 2.

Figure 3:
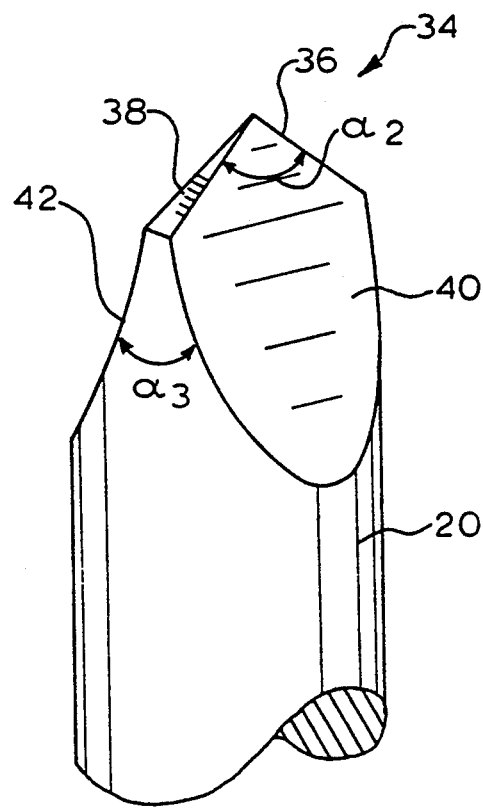
FIG. 3 is a perspective view of the stylet tip in one embodiment of the invention.

Refer now to FIG. 3 which is a perspective view of the stylet 20. As can be seen in the figure, the tip 34 of the stylet 20 includes first and second tip surfaces 36, 38 respectively which form an obtuse angle $a_2$ with respect to one another. In the preferred embodiment, this angle is approximately 110° when the device is used as a bone marrow biopsy needle. The first and second tip surfaces are connected to one another by first and second cutting surfaces 40, 42. The first and second cutting surfaces form an acute angle $a_3$ with respect to one another. Generally, this angle $a_3$ will range from 30° to 60°. The tip surfaces 36, 38 are more clearly illustrated in FIG. 4, and the cutting surfaces 40, 42 are more clearly illustrated in FIG. 5.

Figure 4:
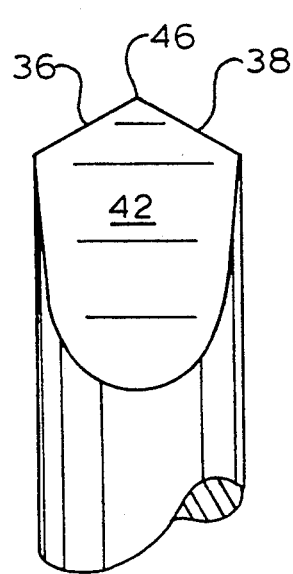
FIG. 4 is a side view of a stylet tip in the preferred embodiment of the invention.
Figure 5:
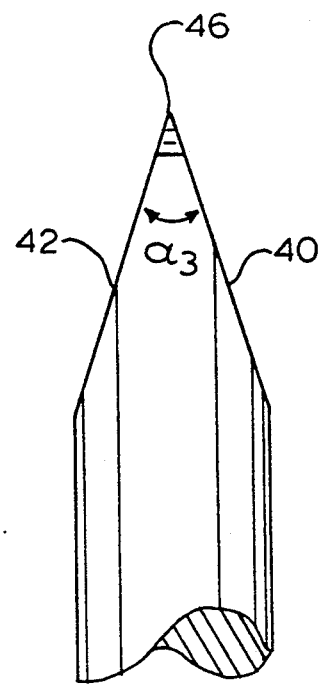
FIG. 5 is another side view of the stylet tip of FIG. 4 when the stylet has been axially rotated 90 degrees.

There are several advantages to having a stylet with two tip surfaces 36, 38 and two cutting surfaces 40, 42. First, the use of four surfaces to define a cutting tool causes each cutting surface to increase the cutting action which occurs when the stylet is axially rotated back and forth. Traditional stylets contain a single cutting surface which has a reduced cutting capability compared to the cutting capability of a stylet having four cutting surfaces. Another advantage of the stylet illustrated in FIG. 4 is that by having a central point 46 at the apex of the stylet defined by the convergence of the tip surfaces 36, 38 and the cutting surfaces 40, 42, the stylet is more easily anchored in the patient's bone and does not tend to wobble as the stylet is rotated back and forth.

Figure 6:
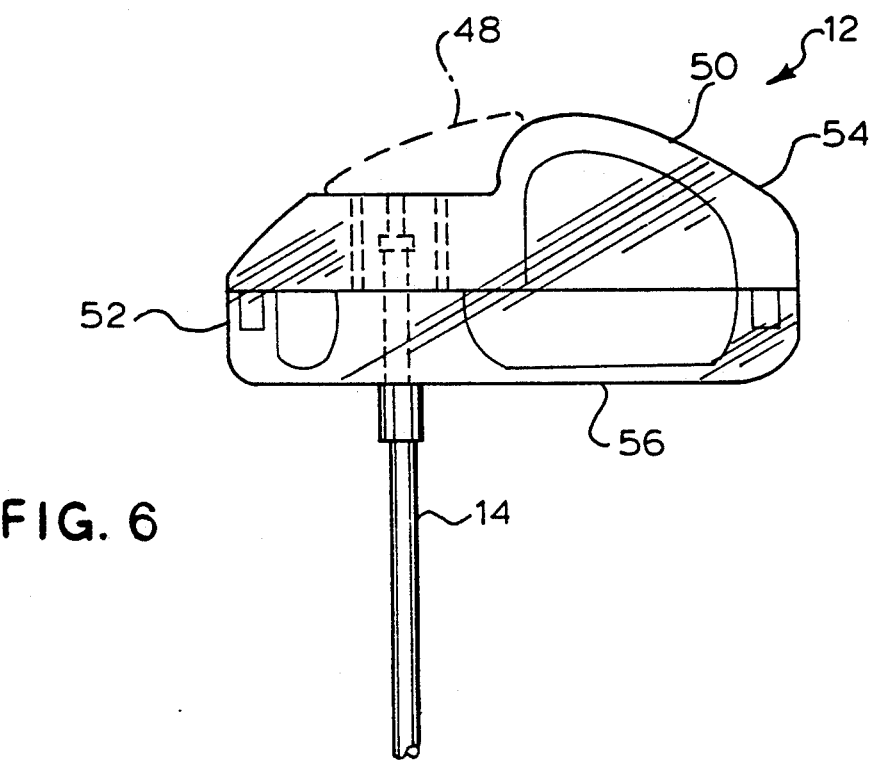
FIG. 6 is a side view of the preferred embodiment of the invention with the stylet shown in phantom.
Figure 7:
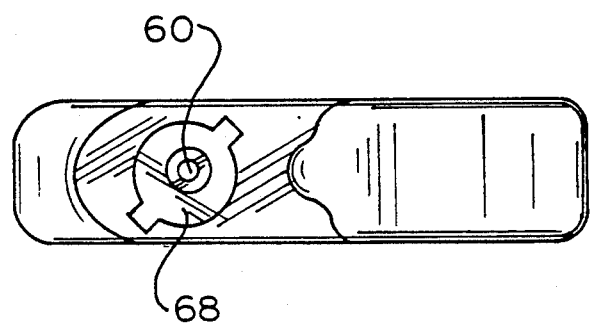
FIG. 7 is an end view of the handle assembly with the stylet removed.
Figure 8:
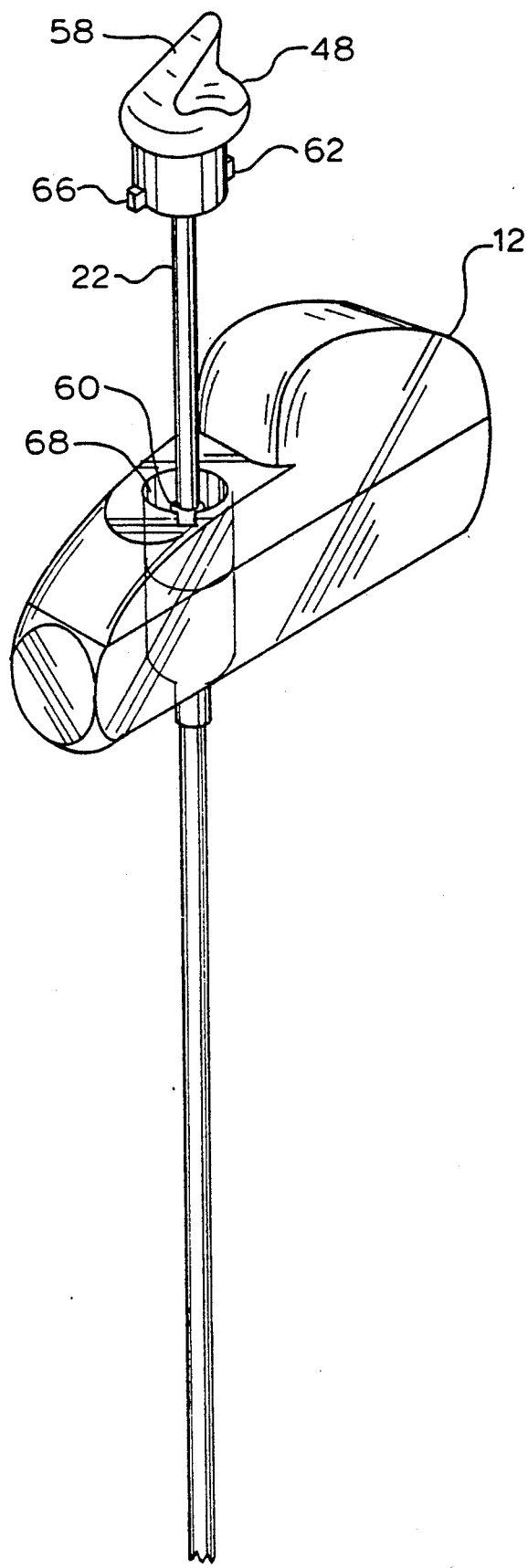
FIG. 8 is a perspective view of the needle assembly with the stylet partially withdrawn from the handle.
Figure 9:
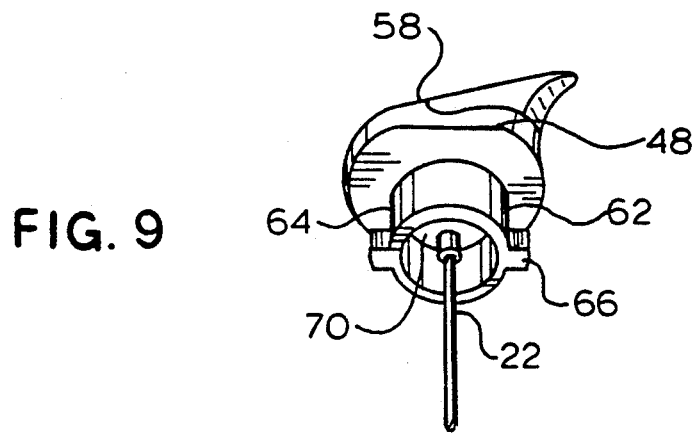
FIG. 9 is a perspective view of the stylet hub and stylet.
Figure 12:
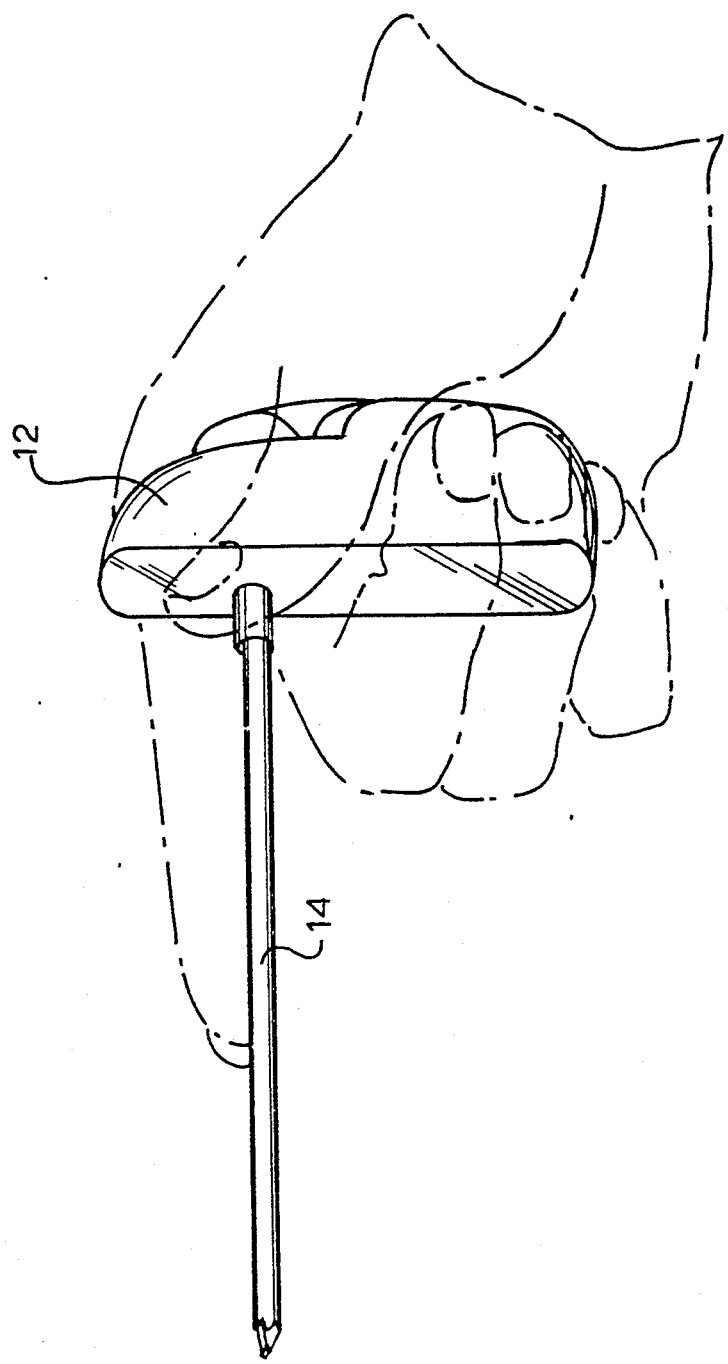
FIG. 12 is a perspective view of a preferred embodiment when it is being used by a physician.

Refer now to FIG. 6 which is a side view of the handle 12 and cannula 14 of the preferred embodiment of the invention with the stylet knob 48 shown in phantom. As can be seen in the figure, the handle 12 has an upper surface 50 having a downward extending off-center radius designed to conform to the shape of a user's palm. The radius is off-center with respect to the width w of the handle and extends downward toward a lower surface 56 of the handle. This off-center radius causes the handle to have a first relatively narrow end 52 and a second relatively wide end 54. The lower surface 56 is also curved in a manner to conform to the shape of a physician's fingers as the physician grasps the lower surface of the handle. This is illustrated in FIG. 12. In the preferred embodiment, the lower surface 56 and upper surface 50 both have a curved radius that is in a plane normal to the off-set radius discussed above.

In the preferred embodiment of the invention, the stylet knob 48 also has an upper surface 58 that has an offset radius that is generally equal to the offset radius of the upper surface of the handle 12. Thus, when the knob is inserted in the handle, the upper surfaces mate with one another to form a relatively smooth working surface for the physician. The handle includes a receiving orifice 60 to receive a downward extending portion 62 of the knob. In the preferred embodiment of the invention, the downward extending portion of the knob has a cylindrical shape 64 and includes at least one outwardly extending prong 66 that mate with a matching keyhole 68 in the receiving orifice 60 of the handle 12. The purpose of the keyhole 68 and prong 66 is to cause the knob 48 to be locked in place when the knob is in a first position and to allow the knob to be removed from the handle when the knob is rotated so that the prong 66 is aligned with keyhole 68. This arrangement provides stability for the upper surface of the handle when the stylet is in place inside the cannula.

In the preferred embodiment, the first end 22 of the stylet is permanently attached to a lower surface 70 of the knob 48. Thus, when the knob is in position in the handle, the stylet extends through the handle and cannula. In the preferred embodiment of the invention the cutting surfaces 40, 42 of the stylet terminate beyond the cutting teeth 26 of the cannula as illustrated in FIG. 1.

One particularly important advantage of the multiple cutting teeth on the cannula and the cutting surfaces on the stylet is that it is not necessary to align the cutting surfaces on the stylet with the cutting teeth on the cannula. Traditional biopsy needle assemblies as shown in U.S. Pat. No. 4,838,282 that have a single cutting surface on the stylet and cannula require that the stylet be carefully aligned with the cannula. This greatly increases the manufacturing cost of the assembly.

One advantage of the invention is that the stylet knob 48 is relatively small. Thus, when it is removed from the handle 12, the radius of the upper surface remains essentially unchanged so that a physician can still easily grasp and rotate the handle while using an index finger to guide the cannula.

Figure 10:
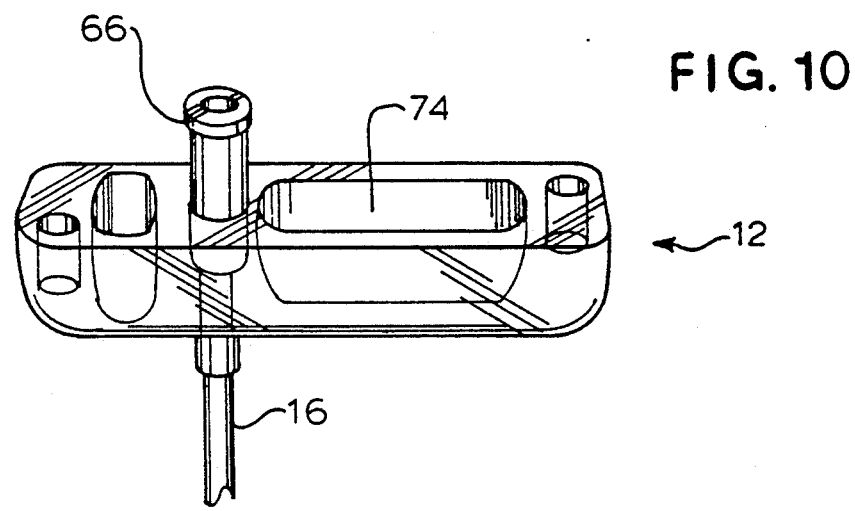
FIG. 10 is a perspective view of the interior of the lower portion of the handle prior to assembly.
Figure 11:
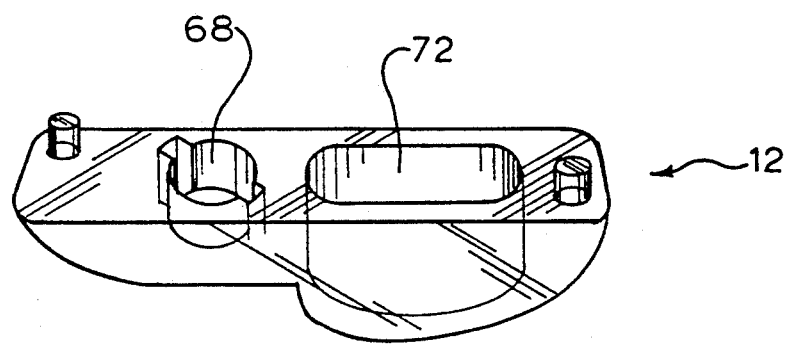
FIG. 11 is a perspective view of the interior of the upper portion of the handle prior to assembly.

Refer now to FIGS. 10 and 11 which are perspective views of an interior portion of the handle 12 prior to assembly. As can be seen in the figures, the handle 12 is actually formed of two pieces of plastic or other material and includes hollow spaces 72, 74 to reduce the weight of the needle assembly. In the preferred embodiment, the upper and lower portions of the handle are snap fit together during assembly so that the hollow spaces are enclosed within the handle and do not interfere with cleaning of the device prior to use.

While the invention has been described in detail and with reference to specific embodiments thereof, it will be apparent to those skilled in the art that various changes and modifications can be made therein without departing from the spirit and scope of the invention.

We claim:

1. A needle assembly, comprising:
a handle;
a cannula, said cannula having a first end connected to said handle and a second end extending outwardly from said handle; and
a removable stylet having first and second ends, said stylet extending through said cannula from said handle, and said second end of said stylet extending beyond said second end of said cannula, said second end of said stylet having a tip having first and second tip surfaces which form an obtuse angle, and first and second cutting surfaces which connect said tip surfaces, said cutting surfaces forming an acute angle.

2. A needle assembly, comprising:
a handle; and
a cannula, said cannula having a first end connected to said handle and a second end extending outwardly from said handle, said second end having multiple cutting teeth, each tooth having at least two beveled edges to cut bone when said cannula is axially rotated back and forth.

3. A needle assembly, comprising:
a handle;
a cannula, said cannula having a first end connected to said handle and a second end extending outwardly from said handle, said second end having multiple cutting teeth to cut bone when said cannula is axially rotated; and
a removable stylet having first and second ends, said stylet extending through said cannula from said handle, and said second end of said stylet extending beyond said second end of said cannula, said second end of said stylet having a tip having first and second tip surfaces which form an obtuse angle, and first and second cutting surfaces which connect said tip surfaces, said cutting surfaces forming an acute angle.

4. A needle assembly, comprising:
a handle, said handle having an upper surface having a downward extending off-center radius to conform to the shape of a user's palm, said downward extending off-center radius having a center positioned off-center with respect to a width of the handle and positioned downward toward a generally planer lower surface of the handle, said downward extending off-center radius producing a first relatively narrow end and second relatively wide end of said handle;
a cannula, said cannula having a first end connected to said lower surface of said handle toward said relatively narrow end and a second end extending outwardly from said handle; and
a removable stylet having first and second ends, said stylet extending through said cannula from said handle.

5. A needle assembly, comprising:
a handle, said handle having an upper surface being a curved surface having an off-center radius to conform to the shape of a user's palm, said off-center radius being off-center with respect to a width of the handle, said off-center radius producing a first relatively narrow end and second relatively wide end of said handle, said handle also having a lower surface;
a cannula, said cannula having a first end connected to said lower surface of said handle toward said relatively narrow end and a second end extending outwardly from said handle; and a removable stylet having first and second ends, said stylet extending through said handle from said upper surface to said cannula, said first end having a knob attached thereto, said knob having an upper surface having an off-center radius generally equal to said off-center radius of said handle to allow said knob to conform to said curved surface of said upper surface of said handle.

6. A needle assembly, comprising:

a handle, said handle having an upper surface being a curved surface having an off-center radius to conform to the shape of a user's palm, said off-center radius being off-center with respect to a width of the handle, said off-center radius producing a first relatively narrow end and second relatively wide end of said handle, said handle also having a lower surface, said handle having a receiving orifice;

a cannula, said cannula having a first end connected to said lower surface of said handle toward said relatively narrow end and a second end extending outwardly from said handle; and a removable stylet having first and second ends, said stylet extending through said handle from said upper surface to said cannula, said first end having a knob attached thereto, said knob having an upper surface having an off-center radius generally equal to said off-center radius of said handle to allow said knob to conform to said curved surface of said upper surface of said handle, said knob having a downward extending surface which mates with said receiving orifice of said handle to allow a portion of said downward extending surface to be inserted into said handle at said receiving orifice.

7. A needle as recited in claim 6 wherein:

said receiving orifice of said handle and said downward extending surface of said knob include a locking means for locking said knob in said handle when said knob is in a first position, and for unlocking said knob from said handle when said knob is axially rotated to allow said knob and stylet to be removed from said handle.

* * * * *